(12) United States Patent
Yazdanfar et al.

(10) Patent No.: US 9,066,657 B2
(45) Date of Patent: Jun. 30, 2015

(54) METHODS AND SYSTEMS OF OPTICAL IMAGING FOR TARGET DETECTION IN A SCATTERING MEDIUM

(75) Inventors: Siavash Yazdanfar, Niskayuna, NY (US); Floribertus Heukensfeldt Jansen, Ballstonlake, NY (US); Stephen Lomnes, Philadelphia, PA (US); Xinghua Wang, Jersey City, NJ (US)

(73) Assignee: General Electric Company, Niskayuna, NY (US)

( * ) Notice: Subject to any disclaimer, the term of this patent is extended or adjusted under 35 U.S.C. 154(b) by 645 days.

(21) Appl. No.: 12/952,359

(22) Filed: Nov. 23, 2010

(65) Prior Publication Data
US 2012/0128264 A1   May 24, 2012

(51) Int. Cl.
| | |
|---|---|
| G06K 9/40 | (2006.01) |
| F21V 9/16 | (2006.01) |
| G01J 1/58 | (2006.01) |
| G01T 1/10 | (2006.01) |
| G21H 3/02 | (2006.01) |
| G21K 5/00 | (2006.01) |
| H01J 65/06 | (2006.01) |
| H01J 65/08 | (2006.01) |
| H01L 27/00 | (2006.01) |
| G01N 21/86 | (2006.01) |
| G01V 8/00 | (2006.01) |
| A61B 5/00 | (2006.01) |

(52) U.S. Cl.
CPC ............. *A61B 5/0059* (2013.01); *A61B 5/0064* (2013.01)

(58) Field of Classification Search
USPC .............................. 382/274; 250/459.1, 208.1
See application file for complete search history.

(56) References Cited

U.S. PATENT DOCUMENTS

| | | | |
|---|---|---|---|
| 6,032,070 A | 2/2000 | Flock et al. | |
| 6,897,954 B2 * | 5/2005 | Bishop et al. | 356/317 |
| 7,383,076 B2 | 6/2008 | Ntziachristos et al. | |
| 7,426,026 B2 | 9/2008 | Matsumoto et al. | |
| 7,599,732 B2 | 10/2009 | Sevick-Muraca et al. | |
| 7,692,160 B2 | 4/2010 | Lee et al. | |
| 7,960,707 B2 * | 6/2011 | Hall et al. | 250/459.1 |

(Continued)

FOREIGN PATENT DOCUMENTS

| | | | | |
|---|---|---|---|---|
| WO | 2006062895 A2 | 6/2006 | | |
| WO | WO2009081969 | * | 2/2009 | H04N 7/18 |

OTHER PUBLICATIONS

Evidence of publication date of US 20110164124 A1 as WO2009081969 (A1) from European Patent Office.*

(Continued)

*Primary Examiner* — Michelle Entezari
(74) *Attorney, Agent, or Firm* — Jenifer E. Haeckl

(57) ABSTRACT

A method for enhancing contrast in fluorescence imaging is provided. The method comprises providing a patterned illumination source for illuminating one or more regions corresponding to a scan step, scanning at least a portion of a surface of a subject using a plurality of scan steps, acquiring image frames corresponding to two or more scan steps, deducting a background fluorescence from the image frames corresponding to the two or more scan steps to form one or more processed image frames, and reconstructing an image using one or more of the processed image frames.

20 Claims, 8 Drawing Sheets

(56) References Cited

U.S. PATENT DOCUMENTS

| | | | | |
|---|---|---|---|---|
| 8,084,755 | B2* | 12/2011 | Hall et al. | 250/459.1 |
| 2005/0281708 | A1* | 12/2005 | Trulson et al. | 422/82.07 |
| 2006/0184043 | A1 | 8/2006 | Tromberg et al. | |
| 2007/0121200 | A1* | 5/2007 | Suzuki et al. | 359/368 |
| 2008/0188736 | A1 | 8/2008 | Bambot et al. | |
| 2008/0296482 | A1* | 12/2008 | Lee et al. | 250/234 |
| 2009/0119808 | A1 | 5/2009 | Giakos | |
| 2009/0240138 | A1* | 9/2009 | Yi | 600/425 |
| 2010/0265516 | A1* | 10/2010 | De Groot et al. | 356/511 |
| 2011/0064296 | A1* | 3/2011 | Dixon | 382/133 |
| 2011/0164124 | A1* | 7/2011 | Hizume et al. | 348/61 |

OTHER PUBLICATIONS http://zeiss-campus.magnet.fsu.edu/print/livecellimaging/techniques-print.html—saved online as early as Jun. 2010.*

Ntziachristos et al.; "Fluorescence Imaging with Near-Infrared Light: New Technological Advances that Enable in Vivo Molecular Imaging"; European Radiology, vol. 13, Issue 1, pp. 195-208, 2003.

Ramanujan et al.; "Multiphoton Fluorescence Lifetime Contrast in Deep Tissue Imaging: Prospects in Redox Imaging and Disease Diagnosis"; Journal of Biomedical Optics, vol. 10, Issue 5, Oct. 21, 2005.

Search Report and Written Opinion from corresponding PCT Application No. PCT/EP2011/070719 dated Mar. 28, 2012.

* cited by examiner

METHODS AND SYSTEMS OF OPTICAL IMAGING FOR TARGET DETECTION IN A SCATTERING MEDIUM

BACKGROUND

The invention relates to optical imaging methods and systems, and more particularly to methods and systems for fluorescence imaging of a light scattering medium.

In vivo imaging of biological tissues facilitates early detection of disease, thereby providing an opportunity for reliable and pro-active diagnosis of diseased tissues. Fluorescence imaging is an example of a powerful non-invasive imaging technique that has been used in various applications in biological sciences. For example, fluorescence imaging is applied in fields such as genetic sequencing, biomedical diagnostics, and flow cytometry. Typically, fluorescence-imaging systems include a light source, which illuminates the subject to be imaged. The tissue inside the subject fluoresces either endogenously or exogenously in response to the excitation illumination, and the resulting emission is imaged to obtain information about the internal composition of the subject.

Fluorescence imaging is generally hampered by poor signal-to-background ratio (SBR) of fluorescent targets located within a subject. Much of this background noise is caused by reflection of the excitation light from the surface, and by strong fluorescence signals emitted from points near the surface of the subject. Different types of fluorescence imaging have been proposed to enhance SBR or contrast in fluorescence imaging. Some of these methods are fluorescence lifetime imaging, multi-spectral and hyper-spectral imaging. Fluorescence lifetime sensitive imaging (FLIM) differentiates various fluorescing species by their relative excited state lifetimes in a time- or frequency-resolved detection. For example, a fluorescence marker has a substantially different fluorescence decay rate than that of the tissue, it is possible to differentiate the two species by FLIM. FLIM reduces the effect of background auto-fluorescence, allowing greater contrast than conventional fluorescence imaging. However, in majority of cases, the difference of lifetime between many existing fluorescence markers and tissue is small, limiting the utility of FLIM.

Multi-spectral imaging has been demonstrated to be able to differentiate auto-fluorescence background and labeled markers for in-vivo applications. Typically, chemometric analysis is used to distinguish spectral signal that originates from the fluorescence marker and tissue auto-fluroescence background since they have distinct features. However, when the concentration of the bio-marker in the tissue is relatively low, unreliable results may be obtained. In addition, such an analysis may result in loss of a substantial amount of signal as only a narrow spectral region of the fluorescence signal is acquired for the analysis. Hence, such an analysis may not be ideal for real time applications.

Accordingly, there is a need for imaging systems and methods that can provide enhanced contrast in fluorescence imaging.

BRIEF DESCRIPTION

In one embodiment, a method for enhancing contrast in fluorescence imaging is provided. The method comprises providing a patterned illumination source for illuminating one or more regions corresponding to a scan step, scanning at least a portion of a surface of a subject using a plurality of scan steps, acquiring image frames corresponding to two or more scan steps, deducting a background fluorescence from the image frames corresponding to the two or more scan steps to form one or more processed image frames, and reconstructing an image using one or more of the processed image frames.

In another embodiment, a fluorescence imaging system for generating an enhanced image of a target in a subject is provided. The system comprises a source configured to illuminate at least a portion of a surface of the subject by a patterned illumination at one or more scan steps, an imaging detector configured to acquire image frames at one or more scan steps, and an imaging processor for processing the image frames to deduct the background fluorescence from the image frames and to reconstruct an image of the target using the processed image frames.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
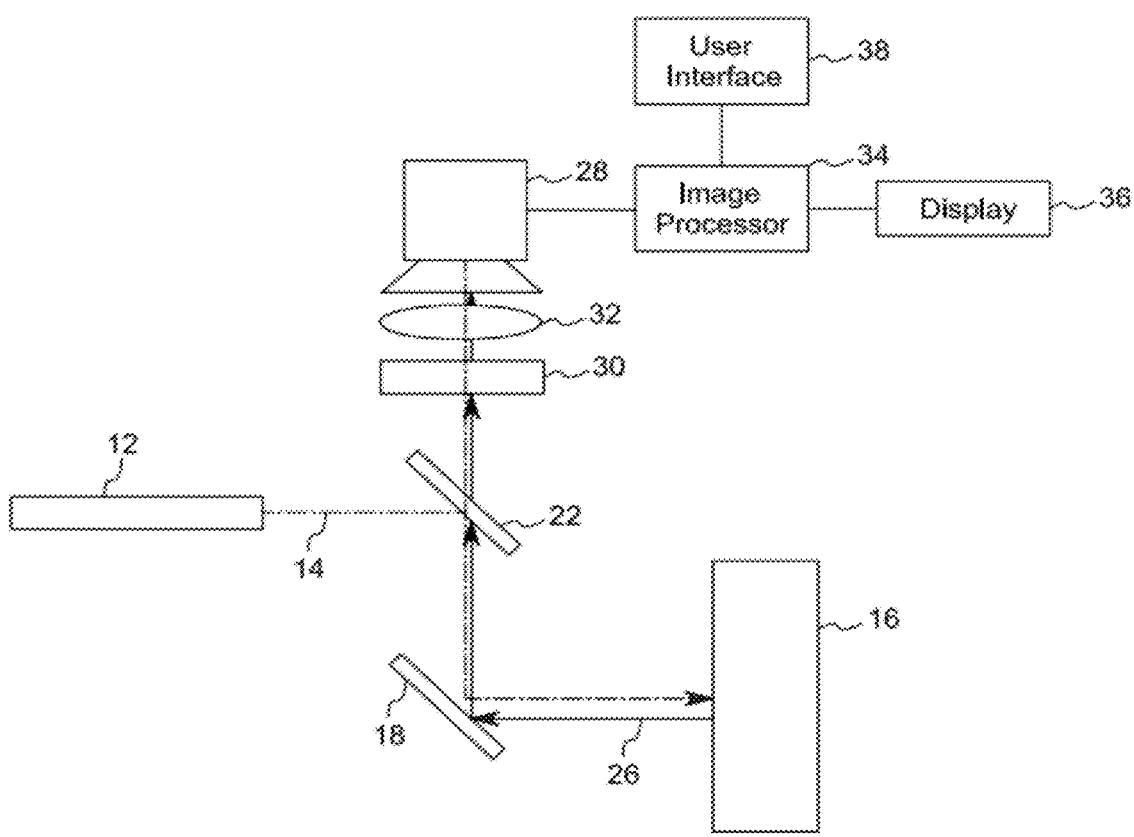
FIG. 1 is a schematic drawing of an example of a fluorescence imaging system.

Described herein are fluorescence imaging systems and methods for enhancing contrast in fluorescence imaging. In one of more embodiments of the invention, a surface of a subject having a scattering medium is illuminated using a patterned illumination and the light emitted by the subject is collected from an illumination region. The light emitted may also be collected from the regions away from the illumination region. As used herein, the term "patterned illumination" refers to light incident on a subject that is to be imaged such that 1) the light is in the form of one or more points that collectively form a determined pattern on a surface of the subject, and 2) the area of the illumination pattern is less than the field of view of the imaging system. In certain embodiments, the method of the invention may comprise providing a patterned illumination source for illuminating one or more regions corresponding to a scan step, scanning at least a portion of a surface of a subject using a plurality of scan steps, acquiring image frames corresponding to two or more scan steps, deducting a background fluorescence from the image frames corresponding to the two or more scan steps to form one or more processed image frames, and reconstructing an image using one or more of the processed image frames.

In one embodiment, the subject is illuminated using a patterned illumination combined with area detection. Area detection comprises detecting emitted light from the illumination region, but more typically comprises detecting emitted light from regions that are away from the illumination regions. The area detection may be performed by employing the techniques disclosed in U.S. Pat. No. 7,692,160 titled "METHOD AND SYSTEM OF OPTICAL IMAGING FOR TARGET DETECTION IN A SCATTERING MEDIUM" which is incorporated herein by reference.

In certain embodiments, the detection area may be about 1 mm to 25 mm away from the illumination region. The distance between the illumination region and the detection area may vary depending on the size of the subject. For example, the distance between the illumination region and the detection area may increase with an increase in size of the subject. When a patterned illumination is incident on a surface of the subject, the target inside the subject fluoresces in response to the patterned illumination or the excitation light, thereby producing emitted light. It should be noted that the terms "patterned illumination" and "excitation light" may be used interchangeably throughout the application. As the distance from illumination region to detection point increases, the amount of reflected light and near-surface fluorescence decreases, reducing the noise and increasing the SBR. A higher SBR improves the detection of emitted light, thereby, increasing the sensitivity of the imaging system. The area detector samples the emitted fluorescence at many different source to detector separations. As used herein, the term "source to detector separation" refers to a distance from a point in the illumination region on the surface of the subject to a point in the area where the emitted light is detected on the surface of the subject. Different distances between the illumination region and the area of measured emitted light provide information about the depth of the target. For the purpose of measuring the distances, the location of the predetermined illumination may be considered to be the geometric center point of the pattern of the patterned illumination, the centroid of illumination intensity, or the closest distance between the source and the detector, depending on the size, shape, and the spatial uniformity of the illumination intensity. Considering a small illumination region on the surface of the subject, the illumination region may have a distribution of intensities; therefore, the distance representation is more likely to be the distance between the centroid of the illumination region and the detector.

The use of patterned illumination allows for deeper penetration of the excitation light as compared to the planar illumination because while employing the patterned illumination the light may be concentrated in a smaller area instead of being spread over the entire imaging surface of the subject, and thus higher local intensity may be used without exceeding average power limits. In one example, full-field imaging techniques may be used for faster imaging time as compared to point-by-point-techniques, where at any given time, only a single point on the surface of the subject, represented by a pixel in the resulting image, is illuminated by the excitation source and the resulting emitted light is detected at another point, or the same point. For point-by-point illumination technique, an image is created by repeating this measurement for all points in the image.

The methods and systems of the invention may be used in a variety of applications such as industrial, small animal, and clinical situations including deep tissue imaging, surgery, and endoscopy. The imaging subject may be illuminated in a reflection mode or transmission mode. While imaging of biological tissue may rely on the natural optical properties of the endogenous molecules for providing optical contrast, in some embodiments, exogenous molecules may be introduced in the tissue to provide additional contrast. In these embodiments, exogenous chromophores as well as fluorophores may be used. Furthermore, the bio-distribution of such contrast agents may be followed. Following the distribution of the contrast agents in the subject, the optics as well as the source may be arranged to illuminate and detect light at one or more wavelengths. For example, the source and associated optics may be arranged to illuminate the surface of the subject with the determined patterned illumination and preferably at an excitation wavelength of a fluorophore, while the detector and associated optics may be arranged to detect light at an emission wavelength of the fluorophore. For example, the system may employ absorbing contrast agents, fluorescence agents, fluorescent gene reporter systems, quantum dots, or phosphor agents. The system may be used with a variety of types of light sources and means for generating patterned excitation. The system may be used in combination with other imaging techniques including X-ray, magnetic resonance imaging (MRI), computed tomography (CT), positron emission tomography (PET), single photon emission computed tomography (SPECT), or the like.

With reference to FIG. 1, an example of a fluorescence imaging system 10 of the invention is illustrated. The system 10 is employed to image biological tissues or the target (not shown) inside the subject 16. The imaging system 10 and the associated method of imaging may be employed to image small or large animals and humans.

An illumination source 12 is used to provide a patterned illumination 14. The patterned illumination 14 is directed towards a subject 16. In one embodiment, the system 10 is configured to determine the depth of the target located inside the subject 16. In one example, the illumination source 14 comprises a plurality of laser diodes. The plurality of laser diodes may be positioned to produce the patterned illumination 14. In another example, a mask may be used in conjunction with the illumination source 14 to produce a desired pattern of the patterned illumination. In one example, the patterned illumination so produced may comprise multiple wavelengths. For example, the source 14 may include laser diodes, so that each laser diode is configured to emit at its own unique wavelength that may be different from the wavelength emitted by the other laser diodes. A multi-wavelength source of light may also be used. In the latter case, ranges of wavelengths or a specific wavelength may be selected by using optical filters, gratings or the like. This selected wavelength(s) may then be allowed to excite the target. In place of laser diodes, the source 14 may comprise one or more of: a continuous wave light source, a pulsed light source (e.g., a pulsed laser), a frequency modulated light source, an intensity modulated light source, a phase modulated frequency varying light source, or combinations thereof. The time and frequency domain methods enable extraction of information on parameters such as fluorescence lifetime, quantum yield, concentration and photon path length. In one example, the illumination source comprises a substantially monochromatic light source.

In certain embodiments, a wavelength of the source 14 may be chosen based upon the fluorophore used for the target tissue. Frequency domain imaging may also be used with the patterned illumination to generate phase data from which the lifetime of the fluorescence may be determined. Fluorescence lifetime allows one to differentiate fluorescent agents, permitting the rejection of auto-fluorescence, and to detect environmental changes, such as pH, around a given agent. This data may then be registered with other imaging modalities, such as computed tomography (CT), to simultaneously provide structural and functional information.

The patterned illumination 14 may be scanned over a portion of a surface of the subject 16. Alternatively, the patterned illumination may be scanned over the entire surface of the subject 16. In some embodiments, the subject 16 may be moved while keeping the patterned illumination spatially constant. In another embodiment, instead of the transverse motion, the subject 16 may be rotated along an axis. In these embodiments, the optics may be configured to adapt to the different tomographic configurations of the subject 16. Acquiring the image data while rotating the subject 16 provides variations in the distance between the surface and the target tissue because of the position of the tissue inside the subject 16 and also because of the change in contours of the subject 16.

The patterned illumination may be scanned over the subject in the form of two or more scan steps. The scanning may be performed by moving the subject, or the source or both, to collect multiple views of the subject. Corresponding image frames may be acquired for the various scan steps. The image frames may be processed to remove the background fluorescence. To reconstruct the image, the processed image frames may be summed together to form a composite image. In one example, the reconstruction methods are used to interpret the two-dimensional (2D) image data into a three-dimensional (3D) representation of the target within the volume.

A portion of the patterned illumination 12 incident upon the surface of the subject 16 may penetrate the outer surface (e.g., skin in case of humans or animals) of the subject 16 and the remaining part may be reflected at the air/skin boundary of the subject 16. A portion of the photons that are propagated within the subject 16 is scattered, and another portion is absorbed and emitted as fluorescence, thereby producing a large number of photon paths. The fraction of the fluorescence light that is not absorbed ultimately exits the subject 16 by diffusing through the skin barrier at various distances from the illumination point. Photons that have traveled deeper in the tissue will take a longer time to exit at the surface of the small animal. In optically homogeneous media the distance between the illumination point and the point at which given photons exit is related to the effective depth of the average path of the photons. Thus the greater the distance between the illumination and exit points the greater the depth will be. Although biological tissues are not optically homogeneous, the distance between illumination points and the point of photon exit is still related to the depth of the average path of photons. Deep penetrating photons emit from areas away from the illuminated region. This in part provides the basis for the area detection of the subject 16, while illuminating only a portion of an exposed surface/area of the subject 16.

In one example, the depth of the target may be determined by varying the distances from the target position in proportion to the target depth and appropriately processing the detected image to determine target depth. As used herein, the term "target position" refers to the position of the projected image of the target on the surface of the subject 16.

The emitted light collected from the subject 16 provides useful information about the optical properties of a region of interest. This information may be extracted and incorporated into image reconstruction algorithms. In certain embodiments, image construction may be improved by the use of an auto-focus system and by obtaining a profile of the scanned regions. Imaging the subject 16, while rotating it along an axis or by moving the subject and the patterned illumination relative to each other, generates a volumetric profile of the subject 16. In these embodiments, a simultaneous acquisition of the image while rotating or moving the subject 16 generates a volumetric profile of the subject 16. This volumetric profile information assists in providing spatial information for image reconstruction and display. Further, the patterned illumination may be dynamically varied while imaging the subject 16. In these embodiments, either of the subject 16 or the patterned illumination may be made to move relative to the other.

As illustrated, the patterned illumination 14 is directed at the subject 16 through associated illumination optics. The optics facilitates the movement of the patterned illumination 14 along the subject 16. In the illustrated embodiment, the patterned illumination 14 is separated from the fluorescence by a spectral separation device, such as a dichroic mirror 22. In one embodiment, the dichroic mirror 22 is a multiple bandpass filter that may be used for simultaneous illumination of the subject 16 at different wavelengths. Further, the dichroic mirror 22 may be configured to reflect a light beam from the illumination source 12 in the form of a patterned illumination in a direction substantially perpendicular to the surface of the subject 16 being scanned. The dichroic mirror 22 directs the patterned illumination 14 towards a beam deflecting device, such as a mirror mounted on a galvanometer 18. The patterned illumination 14 is reflected by the galvo mirror 18 at a predetermined angle and directed towards the subject 16.

In one example, a partial rotation of the galvo mirror 18 may be used to modify the predetermined angle in which the illumination pattern 14 is reflected by the mirror 22 and, consequently reflected by the galvo mirror 18 to a different illumination region on the surface of the subject 16. In some embodiments, successive partial rotations of the galvo mirror 18 may be used to produce a scan. The rotation of the galvo mirror 18 may be done in a stepwise manner, wherein a step rotation of the galvo mirror 18 results in the illumination pattern moving a distance equal to a pitch length of the patterned illumination in a particular direction so that the distance between two nearest neighbors within a patterned illumination is covered by the scan. The "pitch" refers to a distance between two nearest patterns in the patterned illumination. For example, in case of the patterned illumination comprising an array of points, the pitch refers to a distance between two nearest points in a row, or two nearest points in a column. The row pitch may be same or different than the column pitch. As used herein, the term "point" refers to a small area of illumination of the order of 1 mm square. In the case of the illumination pattern comprising a plurality of lines, the pitch is the distance between the two adjacent lines.

In addition to the illustrated optics, other lenses and filters may be employed in the illumination optics to focus the beam at the desired location on the subject 16, and to regulate the intensity of the excitation light, that is the light incident on the subject 16. For example, a lens may be optionally positioned between the galvo mirror 18 and the dichroic mirror 22 so that the galvo mirror 18 is at a focal distance of the lens to provide telecentric imaging. Further, filters may also be positioned between the source 14 and the dichroic mirror 22 to adjust the intensity of the patterned illumination 14 that is incident on the subject 16 so as to avoid any damage to the target disposed inside the subject 16. Other optical components may be employed to generate a plurality of points of illumination from a single source; examples of such components include diffraction gratings and cylindrical lenses, many other methods of generating distinct patterns of illumination are well known in the art.

The system 10 further includes an arrangement for detecting the emitted light 26 that is emitted in response to the excitation light that is the patterned illumination 14. Light 26 emitted from the subject 16 is collected by the collection optics, which may include one or more lenses, mirrors, filters and detectors.

The galvo mirror 18 is oriented to have a descanned imaging detector 28. That is, the emitted light 26 is received at the same position on the detector irrespective of the changing position of the illumination region during scanning the subject 16. For a descanned arrangement for the imaging detector 28, the subject 16 may be moved relative to the imaging detector 28, or the illumination pattern 14 may be moved relative to the subject 16 to scan the subject, or both. In one example, only part of the emitted light (corresponding to a given collection point) impinging on the galvo mirror 18 is reflected at a suitable angle to reach the imaging detector 28. Selective detection of the light from a given collection point may be further enhanced by optically coupling the galvo mirror 18 with lenses and/or filters.

The system 10 comprises a filter 30 configured to block excitation light that is reflected from the surface or from the near surface tissues of the subject 16 from reaching the collection optics. The filter 30 is employed to further reduce the noise in the acquired image signals. The filter 30 may include one or more of: a wavelength specific filter, a polarizing filter, a neutral density filter and/or a spatially varying filter. The filter 30 may cover the entire area of the subject 16 from where the emitted light 26 is collected. In the illustrated embodiment, the optical filter 30 is disposed in the collection path. The optical filter 30 is disposed before the imaging lens 32 and the detector 28.

At a given time during scanning of the surface of the subject 16, the emitted light 26 emerging from the entire upper surface of the subject 16 may or may not be in response to the patterned illumination 14 scanning the entire upper surface of the subject 16 at a given time. For example, in one embodiment, only a portion of the upper surface of the subject 16 may be illuminated with the patterned illumination 14, but the emitted light 26 may be collected from illuminated regions as well as from an area of interest away from the illuminated region. In fluorescence imaging, most of the noise is contributed by reflections of the excitation illumination and also from fluorescence near the surface of the subject. The patterned illumination 14 of the surface of the subject 16, accompanied by detection of the emitted light from areas away from the illumination region, enables collection of a relatively smaller amount of noise than where the emitted light is collected from only the illuminated surface. Collecting the emitted light 26 from areas away from the illumination region decreases contribution from near surface fluorescence around the areas of interest, increases the sensitivity of detection at the depth of the target, even in presence of a background signal. In certain embodiments, the detector 28 is configured to detect an area around and away from the illuminated region.

The detector 28 may be a one dimensional (1D) detector. Using a 1D detector allows for higher frame rates. Although 2D detectors may also be employed. In one example, the detector 28 may comprise one or more of: a charged coupled device, an intensified charged coupled device, a time-gated charged coupled device, a gain-modulated charged coupled device, a complementary metal oxide semiconductor device, an electron bombardment charge coupled device, and an image intensifier tube. Further, intensified, gated, and modulated image intensifiers offer a convenient means for sampling large areas with appropriate temporal measurements.

The detector 28 may capture image frames corresponding to two or more scan steps traversed by the illumination pattern 14 while scanning the surface of the subject 16. A series of such image frames may be acquired to obtain multiple views of the subject 16 or to capture images corresponding to different relative positions of the subject 16 and the patterned illumination 14. An image of the reflected patterned illumination may be used to determine the size and shape of the target. Further, the topology of the subject 16, the patterned illumination, and the fluorescence emission may be used as inputs to a reconstruction algorithm to determine the location and concentration of the target.

In one example, the imaging detector 28 may provide spatial resolution enabling simultaneous detection of optical signals emanating from different locations on the surface of the subject 16. Further, while using an illumination source 12 with multiple wavelengths, the CCD camera may facilitate dividing the light into constituent wavelengths at each given point on the surface of the subject 16. The intensity of the light from the source 14 may be varied depending upon the sensitivity of the detector 28 while remaining below levels that may cause damage to the tissue in the subject 16. In cases where the subject 16 is moved relative to the detector 28, the reconstruction is generally needed to obtain the 2D information on the subject 16.

The system 10 also includes an imaging processor 34 that processes the image frames acquired at various scan steps. Processing of the image frames may comprise deducting background fluorescence from one or more image frames. In one example, illumination regions, other than the one comprising the target, are used to assess background fluorescence.

The imaging processor 34 may employ algorithms to process the image frames and reconstruct the image. The processor 34 may be operatively coupled to a display 36 for displaying the reconstructed image. The processor 36 may be configured to process the images in real time. The processor 36 may also be able to store the image data in a memory, to be processed later. The image processor 36 may be configured to receive inputs from a user using the user interface 38. For example, the user may provide instructions specifying the range where the data in the image frame needs to be processed. Further, the user may specify the empirical equation to be applied for fitting the data. The processing of the image frames and subsequent reconstruction may be based on user commands. The user interface 38 may be a touch screen, allowing the operator or user to select options by touching displayed graphics, icons, and the like.

In certain embodiments, instead of using a detector at a fixed source-detector separation, a camera may be used to image the entire sample surface. Imaging the entire sample surface may be similar to having multiple detectors and thus multiple source-detector separations, allowing for instantaneous imaging of the different depths probed by the excitation light, as well as the rejection of light away from a fluorescent target in the sample. The distance, relative to the excitation, at which light emerges from a turbid medium, is related to the optical properties of the tissue and thus the penetration depth of the light. In certain embodiments, near surface background fluorescence is selectively reduced in order to enhance sub-surface target fluorophores.

In another arrangement of system 10, the detector may have a fixed position relative to the subject. This may be achieved by positioning a galvo mirror in the illumination path but not in the imaging path. This arrangement may use a two dimensional (2D) detector. The target is stationary relative to the detector during operation. The fluorescence pattern on the detector is moved. The advantage of this method is the raw image frame contains 2D information on the target; however, the overall frame rate of the system is limited by the detector frame rate, as an entire image has to be recorded for each scan position of the excitation beam. A large amount of data is collected with this configuration and the data processing is data intensive.

Physiological information about the sample, such as absorption and scattering properties may be measured and modeled with photon transport equations. Constant detector and source separation distance is the basis for conventional detector source separation measurements widely used in diffuse optical imaging. The detector and source separation is a meaningful control parameter in such a system, because at different separation distances, the photon migration paths are different and can penetrate different thickness in the sample.

Figure 2:
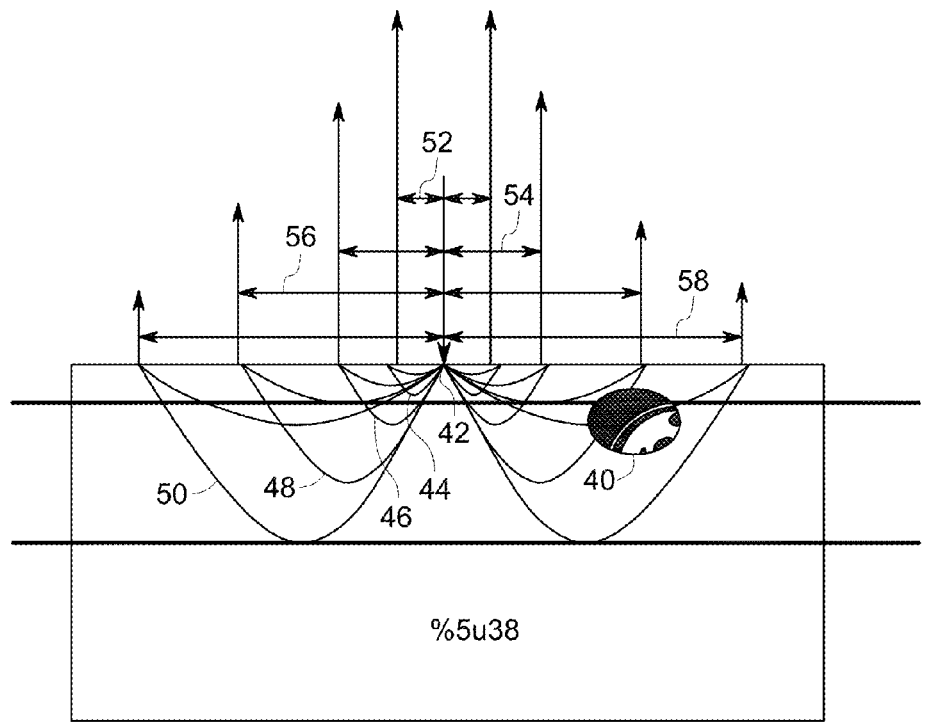
FIG. 2 is a schematic drawing of an example of a location of maximum sensitivity in terms of distance between a source and a target, and detector and the target with respect to the target depth.

A two-dimensional (2D) view of a subject 38 is illustrated in FIG. 2 as a vertical, or a sagittal, cross-section through the subject and the target. The subject 38 includes a fluorescence target 40 to be detected. The target 40 is disposed at a certain depth within the subject 38. The excitation light 41 is emitted from a point source 42 for a 2D representation. For a three-dimensional (3D) representation of the subject 38, the source 42 can be visualized as a line of illumination across the surface of the subject 38, going into the plane of the paper at the point 42. The excitation light penetrates at varying depths as illustrated by the light paths 44, 46, 48 and 50. Depending on the depth of penetration of the corresponding excitation light, the emitted light emerges, on average, from the subject 38 at different distances from the point source 42 as represented by the reference numerals 52, 54, 56 and 58. Therefore, area detection of the emitted light provides information about the depth of the target by enabling detection of emitted light from areas away from the illumination region, such as point 42, of the illustrated embodiment with the detection of emission from many different sources to detector separations. Each pixel at a different distance from the source interrogates a different depth in the subject.

In a two-dimensional (2D) model of a scattering and absorbing tissue phantom with the two dimensions representing a line on the imaging surface and depth, the excitation source is represented as a single point. The model then predicts the emission at a line along the surface of the phantom model, each point representing a different source to detector separation.

Figures 3, 4:
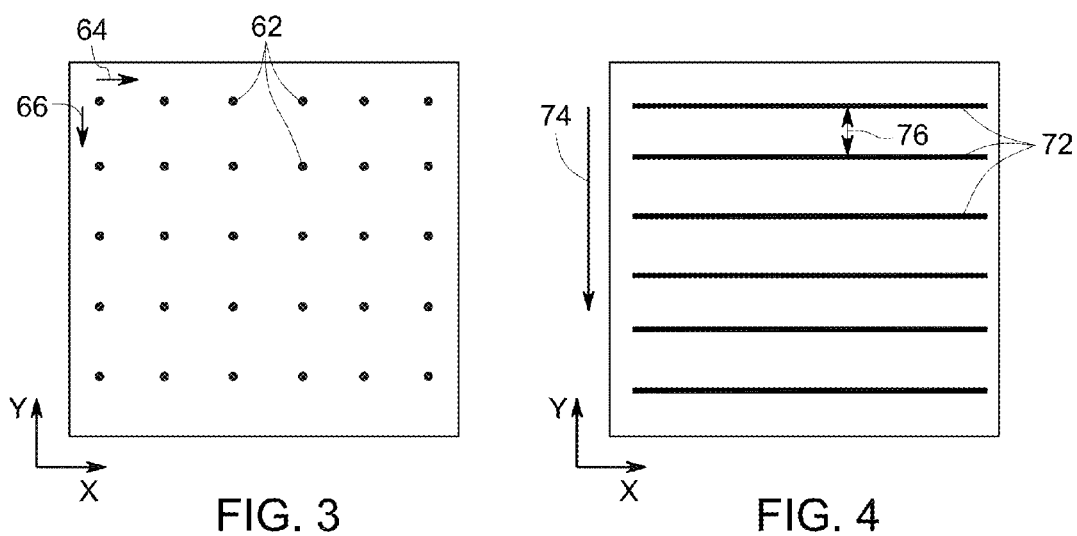
FIG. 3 is an example of a two-dimensional view of a subject being exposed to a patterned illumination comprising an array of point sources.
FIG. 4 is an example of a two-dimensional view of a subject being exposed to a patterned illumination comprising a plurality of line sources an array of line sources.

FIG. 3 illustrates a patterned illumination 60 comprising an array of point illuminations 62. A surface of a subject may be scanned by alternately moving the patterned illumination 60 in a x-direction (as represented by arrow 64) and a y-direction (as represented by arrow 66). Moving the patterned illumination in this manner enables coverage of unit areas formed by joining the nearest neighbors, as represented by the reference numeral 68. Each movement by the patterned illumination corresponds to a scan step.

FIG. 4 illustrates a patterned illumination 70 comprising a plurality of line illuminations 72. As illustrated by arrow 74, the patterned illumination 70 may be moved in the y-direction to scan the area of the subject. Each scan step may be equal to the pitch 76, which is a distance between adjacent line illuminations 72.

Figure 5:
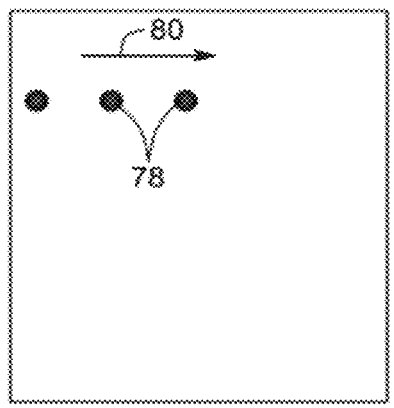
FIG. 5 is an example of a two-dimensional view of a subject being exposed to a patterned illumination comprising a point source, where the point source is scanned over a portion of the surface of the subject.
Figure 6:
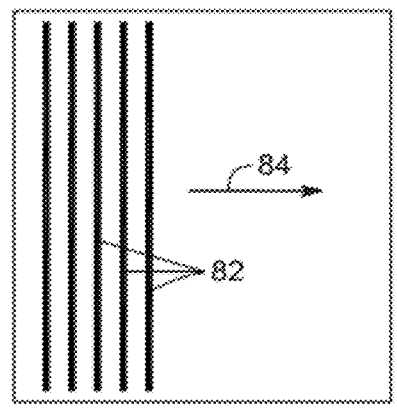
FIG. 6 is an example of a two-dimensional view of a subject being exposed to a patterned illumination comprising a line source, where the line source is scanned over a portion of the surface of the subject.
Figure 7:
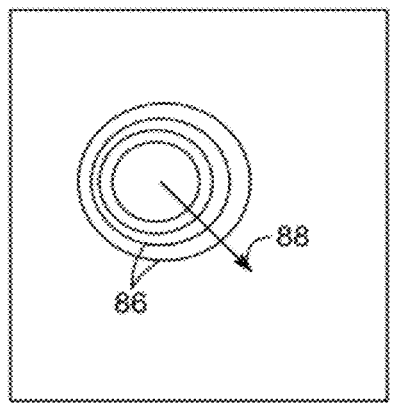
FIG. 7 is an example of a two-dimensional view of a subject being exposed to a patterned illumination comprising a circular pattern, where the circular source is scanned over a portion of the surface of the subject.
Figure 8:
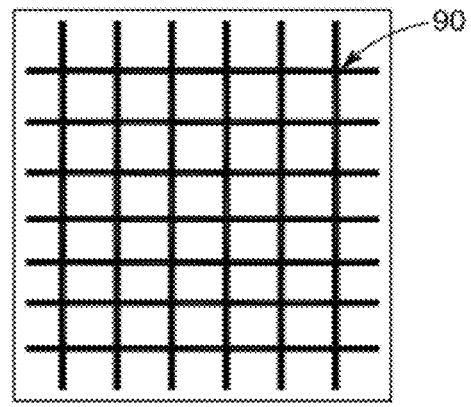
FIG. 8 is an example of a two-dimensional view of a subject being exposed to a patterned illumination comprising a grid pattern, where the grid pattern is scanned over a portion of the surface of the subject.

FIG. 5 illustrates a patterned illumination having point illumination 78 that is moved in a direction represented by arrow 80. The movement of the point illumination 78 enables scanning of the determined portion of the surface of the subject. FIG. 6 illustrates an illumination pattern having a line illumination 82. The subject is scanned by moving the line illumination 82 in a direction represented by the arrow 84. FIG. 7 illustrates a patterned illumination having circular patterns 86 which may be moved in a direction illustrated by arrow 88 to scan the surface of the subject. FIG. 8 illustrates a patterned illumination comprising a grid pattern 90. A grid pattern reduces the number of scanning position on the surface as opposed to a single point illumination on the surface. A certain minimum separation (pitch) between the neighboring points is preferred to avoid cross talk between adjacent spots.

It should be noted that the different patterns, such as points or lines that contribute to the patterned illumination may have same or different intensity of illumination. Further, the different patterns of the patterned illumination may be the same or different in size and shape. For example, in a patterned illumination comprising an array of illumination spots, some spots may be circular, while others may be rectangular or other suitable shapes.

Figure 9:
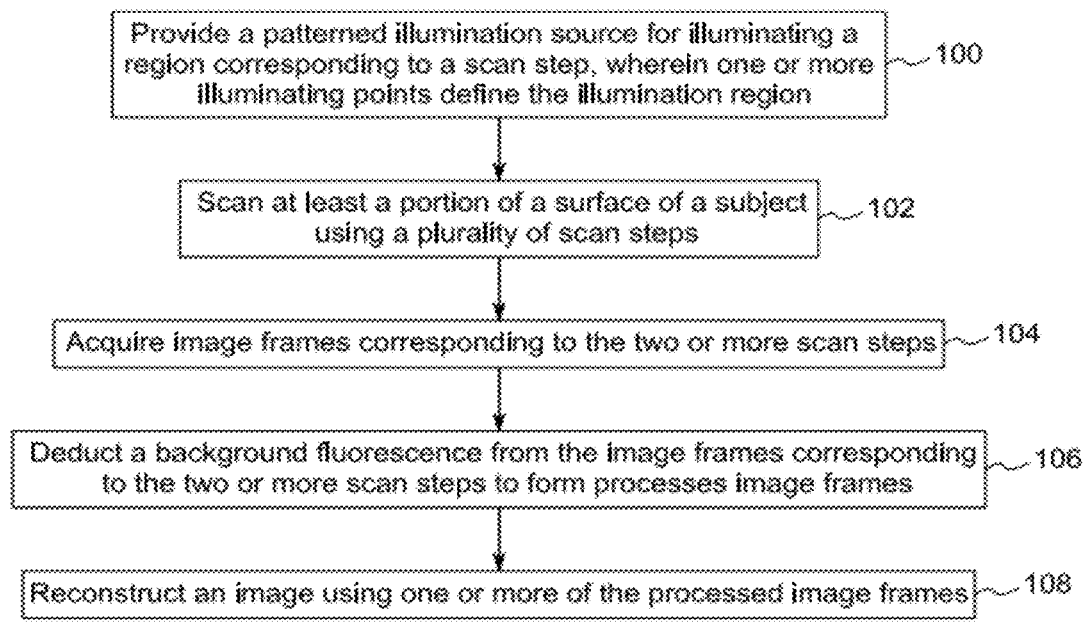
FIG. 9 is a flow chart of an example method of the invention for enhancing contrast in fluorescence imaging.

FIG. 9 is an example of a method for enhancing contrast in fluorescence imaging. At step 100, a patterned illumination source is provided for illuminating a region corresponding to a scan step, where one or more illuminating points define the illumination region. One or more illumination regions may be required to cover the surface of the subject during scanning. An image frame may be generated corresponding to each scan step or illumination region. When a given method uses a plurality of illumination regions, at least one of the illumination regions may comprise a target and the other illumination regions may be used, for example, to assess background fluorescence.

The illumination region may be illuminated by a patterned illumination, where the patterned illumination comprises a point, an array of points, a line, an array of lines, a grid, a non-solid pattern extending along the surface, or combinations thereof. In one example, a contrast agent may be introduced into the scattering medium of the subject.

At step 102, at least a portion of a surface of a subject may be scanned using a plurality of scan steps. The scanning may be done by varying the location of the illumination region with respect to the subject. In one embodiment, varying the location of the illumination region comprises moving the subject relative to the illumination source. In another example, the patterned illumination may be moved with respect to the stationary subject.

In one example where a laser is used as an illumination source, the laser line position moves on target at a distance corresponding to 1 pixel on the detector for each image frame. However, to achieve higher overall frame rate, the scanning speed may be slightly higher than 2 pixels/frame or even 4 pixels/frame without introducing significant artifacts in the final images.

At step 104, image frames corresponding to the scan steps may be acquired. In one example, the image frames may be acquired using a 1D detector. The image frames may be acquired while varying relative positions of the illumination region and the subject, wherein each of the plurality of image frames corresponds to a particular position of the illumination region at a particular scan step. In one embodiment, acquiring the image frames comprises descanning the image frames corresponding to the scan steps. The image frames are received at the same position in the detector.

At step 106, background fluorescence is deducted from the image frames corresponding to the two or more scan steps to form processes image frames. The background fluorescence may be expressed as an empirical equation. In one embodiment, the emitted fluorescence spectrum is fitted with an empirical equation and the equation is deducted from the emitted fluorescence spectrum to obtain fluorescence corresponding to the fluorescent target. In one embodiment, the empirical equation may replicate the illumination spread of the illumination source for a certain position of the patterned illumination on the surface of the subject. Non-limiting examples of empirical equations comprise a Lorentzian fit, a Gaussian fit, and a polynomial fit.

Image frames are recorded for one or more locations of the patterned illumination on the subject. A simulated image may be generated using a forward model for each combination of target depth and illumination region position. The correlation of the detected image to the various simulated images results in peak correlation where the depth of the simulated target represents the best estimate of the depth of the actual target. Some optimal source to detector distances may produce higher correlation values due to the detectability and depth of the actual target. The fitting order may not change the contrast of the image by any significant amount. However, the algorithm becomes much slower as higher order data fitting takes more time. Hence, a simple second order polynomial fit is sufficient for high contrast imaging while minimizing additional processing time. A similar problem may be posed with a computer simulation that predicts the resulting image from a target at some depth.

At step 108, a composite image is reconstructed using one or more of the processes image frames. Reconstructing the image may comprise summing together the processed image frames to generate a composite image. In one embodiment, a noise reduction algorithm may be used prior to or as a part of image reconstruction.

Figure 10:
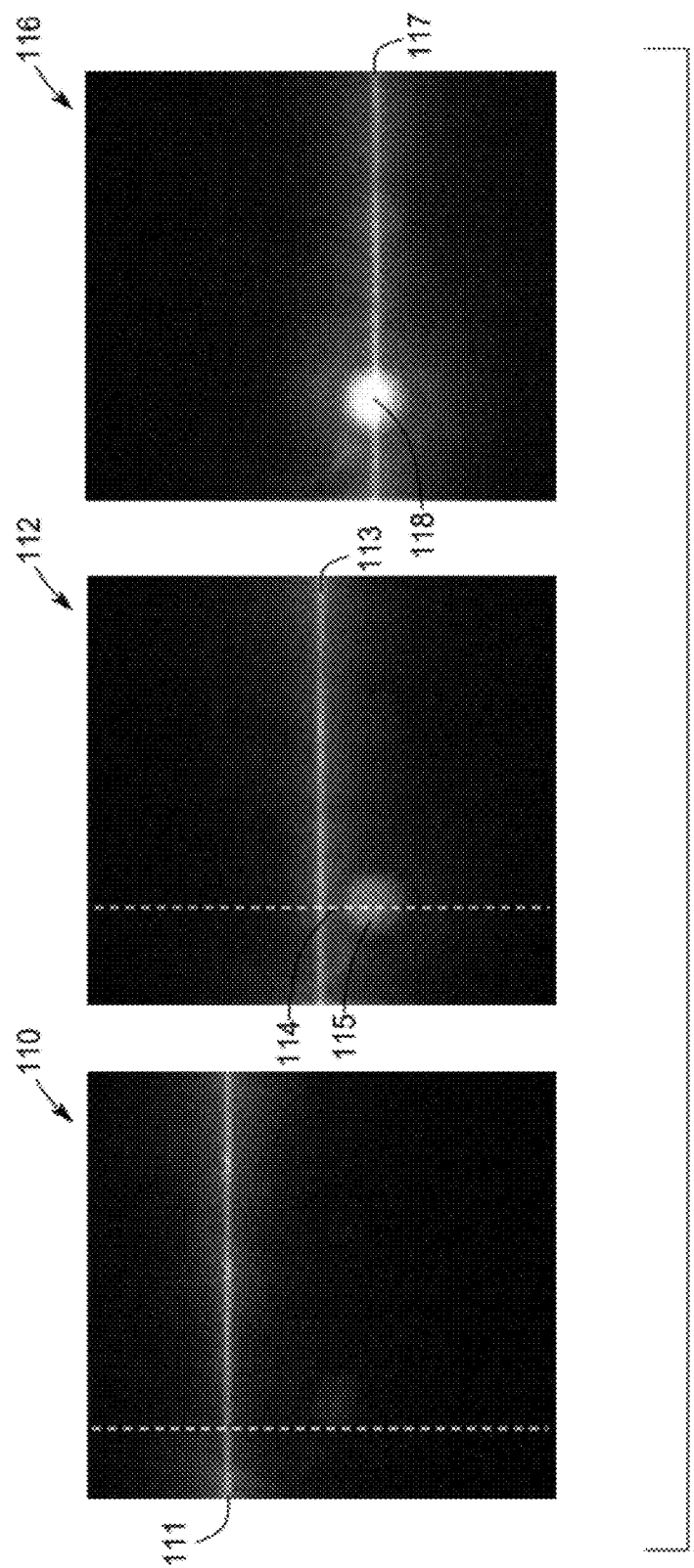
FIG. 10 is a two-dimensional view of a subject being exposed to a patterned illumination comprising a line source.

FIG. 10 illustrates an example of a scanning step for scanning the illumination pattern across a surface of a subject having a target. One image frame for each scanning position may be collected. A series of image frames corresponding to different illumination scanning positions are obtained. For a line illumination pattern, a simple linear scan is most suitable for adequate sample coverage. In the illustrated embodiment, the three image frames correspond to three different lateral positions of the illumination source, such as a laser, scanning across the fluorescence target. In the illustrated embodiment, first image frame 110 comprises background fluorescence 111, the second image frame 112 comprises background fluorescence 113 and fluorescence 114 from the target dye 115 and the third image frame 116 comprises background fluorescence 117 and fluorescence 118 from the target dye 115.

Figure 11:
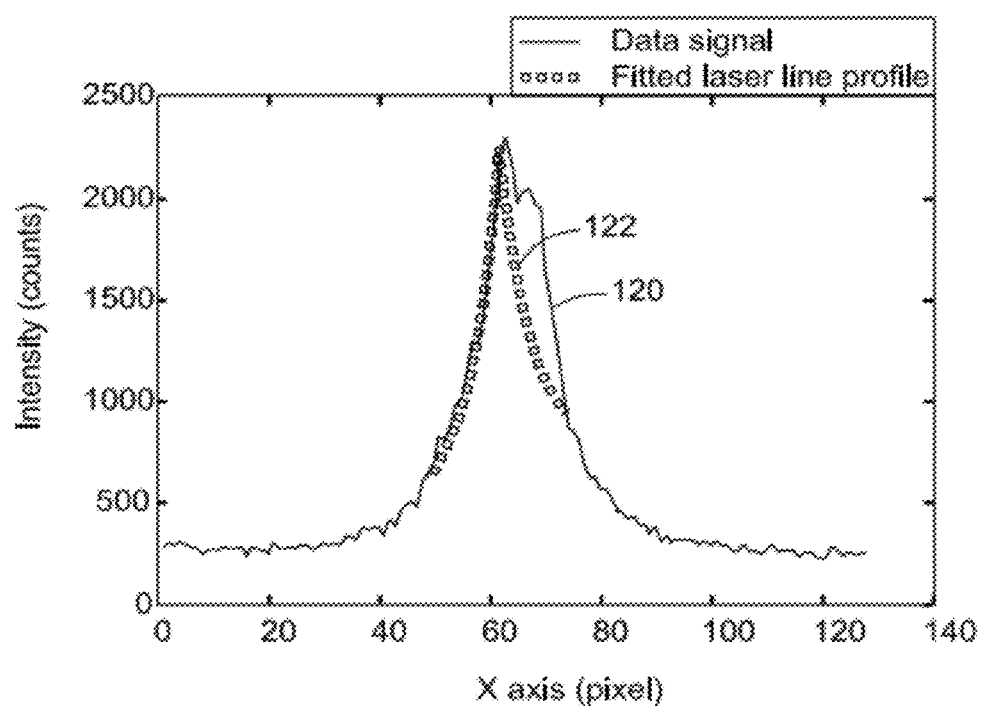
FIG. 11 is a graph for reducing background fluorescence from the excitation signal to obtain the actual fluorescence from the fluorescence marker of interest.

FIG. 11 corresponds to an example step for deducting the background fluorescence from the fluorescence spectrum. An excitation spread function is obtained for the excitation source. A background fluorescence pattern is generated from the raw data by reducing the excitation spread from the measured images at each position. In one example, to fit the laser intensity profile accurately, the background pattern is obtained for a smooth sample where only fluorescence background, and no target, is present. Curve 120 represents the measured fluorescence signal corresponding to an illumination region. Curve 122 represents a second order polynomial that is used to approximate the excitation spread function 120 (such as a line spread function). The fitted curve 122 is subtracted from the measured fluorescence signal 120, and the result is the processed fluorescence signal from the sample. The remaining spectrum post reduction is the target fluorescence signal from the fluorescent target. The difference between the collected fluorescence signal and the fitted laser line profile represents the total amount of fluorescence signal from the target, but not any background.

Figure 12:
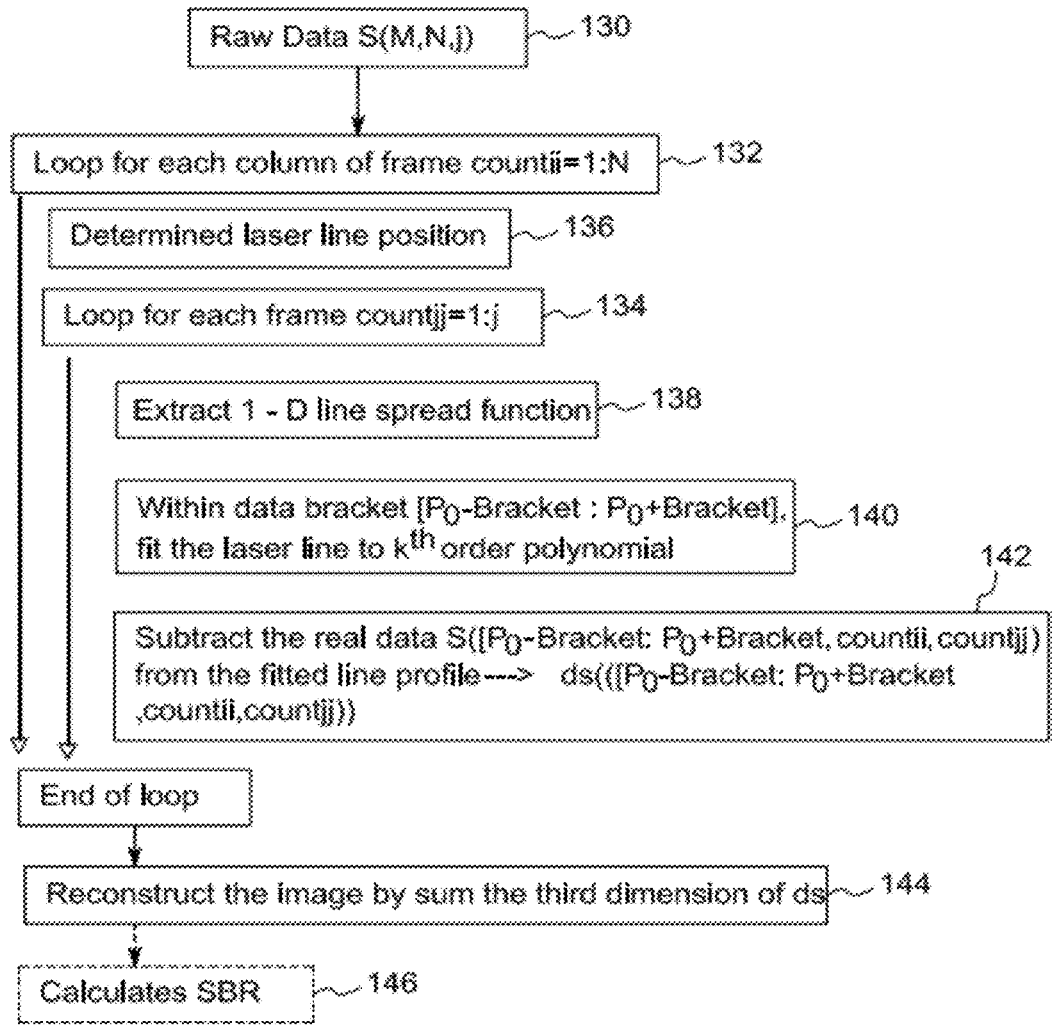
FIG. 12 is an example algorithm for enhancing contrast in fluorescence imaging.

FIG. 12 illustrates an example algorithm for obtaining enhanced fluorescence imaging by reducing the background fluorescence from the emitted fluorescence intensity. In this example, the patterned illumination comprises an array of illumination points. At step 130, the raw data, comprising a number (j) of images collected on the image detector, is provided as an input to the imaging processor of the imaging system. This data may be entered into the imaging system using, for example, the user interface. The size of the raw image data is defined to be M×N, where M is the number of illumination points along y-axis, and N is the number of illumination points along x axis. The raw data set may be a three dimensional cube with size M×N×j, or S(M,N,j). The number of image frames to be collected is determined by the desired scanning speed of the illumination source. As a non-limiting example, the scanning speed of the laser line may be about 1 pixel/frame, whereby, the position of the patterned illumination traverses the subject at a distance corresponding to 1 pixel on the detector for each image frame. However, to achieve a higher overall frame rate, the scanning speed may be slightly higher than 2 pixels/frame or may be 4 pixels/frame without introducing significant artifacts in the final images. For a scanning rate of 1 pixel/frame, the number of total frames, j, may be equal to number of pixels along a determined axis, such as pixels along a y-axis, represented by M.

At steps 132 and 134, iterations are performed for each row and column in the array of the patterned illumination, and corresponding image frames are acquired. Iterations for the columns are represented as countii, and iterations for the rows are represented as countjj in the raw data sets. At step 136, the algorithm first determines the laser line position on the image frame P0. At step 138, a profile of the raw image data set S(P0−Bracket: P0+Bracket,countii,countjj) is extracted, where the Bracket is the number of data points on each side of the peak that are selected to perform the fitting for the peak. In one example, the profile may be a one-dimensional profile. The 1-D profile is fitted by a $k^{th}$ order polynomial, and then the raw data is subtracted from the fitted profile.

At step 140, the residual is stored in dS(P0−Bracket: P0+Bracket,countii,countjj), which represents the pure fluorescence signal from target. At step 142, the processed image frames are summed together to generate a composite image. The result is simply the background subtracted 2-D image fluorescence F(M,N).

Several data processing parameters may be used to influence or modify the final image quality, for example, the choice of the fit function, the fitting order (in the case of a polynomial), and the size of the data bracket chosen to perform the data fitting. With the aforementioned method, higher contrast may be obtained as compared with conventional wide field imaging method. Optionally, at step 144, SBR may be calculated for the composite image.

To increase the overall frame rate of the system, the scanning rate of the laser may be increased from a standard rate of 1 pixel/frame to a slightly higher rate. Higher scanning rates increase the speed of overall image acquisition.

The methods and systems of the invention may be used, for example, for real time fluorescence imaging applications. In one embodiment, the methods may be used to enhance contrast of images acquired during fluorescence image guided surgery procedures.

EXAMPLES

Figure 13A:
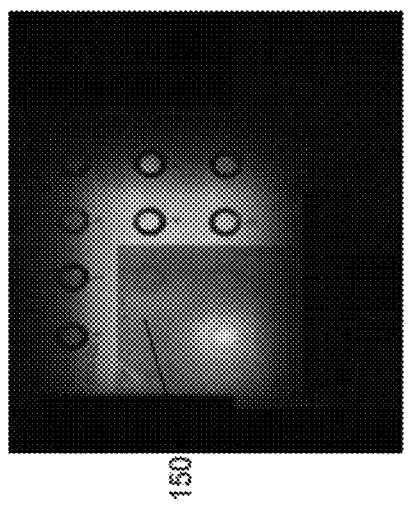
FIG. 13a is a wide field fluorescence image of a sample having a selected region of interest, where the wide field fluorescence image is rendered in grayscale.
Figure 13B:
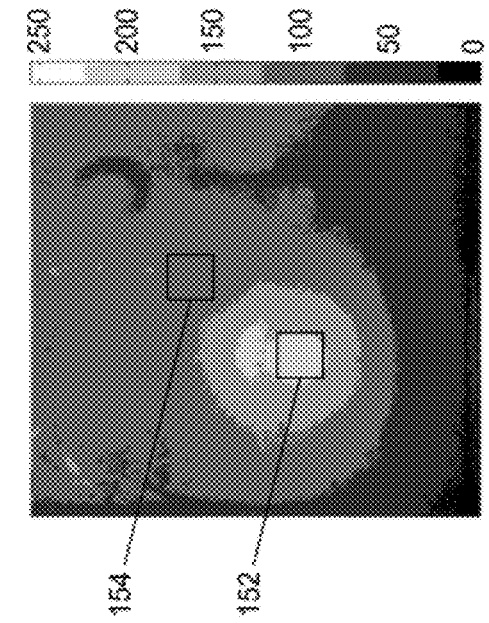
FIG. 13b is a wide field fluorescence image of the selected region of interest in the sample of FIG. 13a, where the wide field fluorescence image is rendered in false color (shown in grayscale)
Figure 13C:
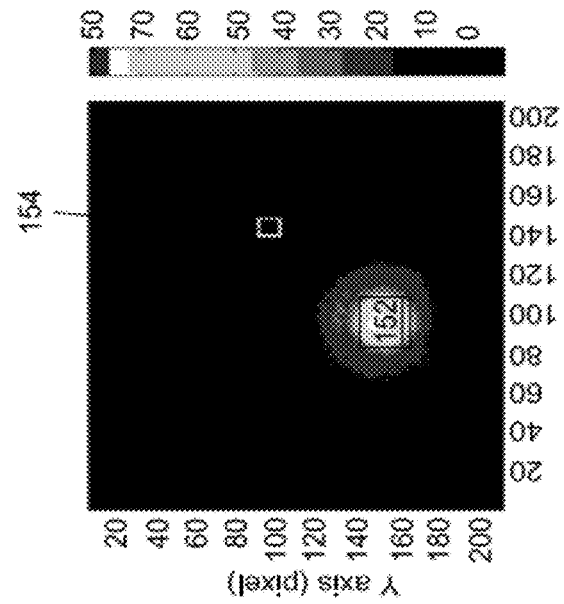
FIG. 13c is a processed image of the selected region of interest.

Comparison of wide field image with ACF processed image is provided. A cover block having a thickness of about 2.5 mm with Cy5.5 1.5 nm is used. FIG. 13*a* illustrates a wide field image rendered in grayscale. FIG. 13*b* illustrates a wide field image rendered in false color (shown in grayscale) for selected region of interest. FIG. 13*c* illustrates ACF processed image for selected region of interest 150.

The first sample contains a 5 mm target with 1000 nM of Cy5.5 dye. The target is covered with a cover piece of 2.5 mm thick with 1.5 nM Cy 5.5. In FIG. 13*a* a pseudo wide field fluorescence image is collected by scanning the laser line at speed substantially higher than the frame rate of the camera. This image is effectively equivalent to a conventional fluorescence image. The data was collected with 7.5 mw of laser power at 635 nm excitation. Fluorescence images were collected using an EMCCD (Hamamatsu ORCA C4742) with intrinsic resolution of 1344×1024 with 2×2 binning, resulting in 672×512 effective pixels. The electron multiplier gain was set at 255, with a shutter speed of 50 ms/sec.

In FIG. 13*b*, the image of FIG. 13*a* is cropped for the selected region of interest, and false color rendering is applied to the image. If ROI 152 and 154 are selected as the signal and background region, the contrast and signal-to-background ratio of the image can be calculated to be 0.40 and 1.33, respectively. The contrast of the image is poor, and light diffused from the target make the target looks bigger than the real size.

After application of the aforementioned background subtraction algorithm, the contrast increased to 0.93 and the signal-to-background ratio improved by over an order of magnitude to 28.5. The halo around the image is significantly reduced and image quality is substantially better than conventional wide field fluorescence image.

To study the influence of the depth of the target to the processing algorithm, a 5 mm thick cover piece is used. A thicker cover piece caused very strong diffusion of the light and substantially reduced contrast, although the dye concentration in the cover piece remains the same. With background subtraction, the processed image improved the contrast from 0.32 to 0.85, and the signal-to-noise background improved from 0.85 to 13.1.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for enhancing contrast in fluorescence imaging, comprising:
   providing a patterned illumination source for illuminating one or more regions corresponding to a scan step;
   scanning at least a portion of a surface of a subject using a plurality of scan steps;
   collecting an emitted light from an illuminated region as well as from an area of interest away from the illuminated region;
   acquiring image frames corresponding to two or more scan steps;
   deducting a background fluorescence from the image frames corresponding to the two or more scan steps to form one or more processed image frames, wherein the background fluorescence is based on an excitation spread function; and
   reconstructing an image using one or more of the processed image frames.

2. The method of claim 1, wherein the step of deducting comprises:
   collecting an emitted spectrum from a first illumination region;
   collecting an excitation spread function for the first illumination region; and
   deducting the excitation spread function from the emitted spectrum.

3. The method of claim 1, wherein an illumination the illuminated region is illuminated by a patterned illumination, and wherein the patterned illumination comprises a point, an array of points, a line, an array of lines, a grid, a non-solid pattern extending along the surface, or combinations thereof.

4. The method of claim 1, wherein at least one illumination region comprises a target, and wherein one or more non-target illumination regions are used to assess the background fluorescence.

5. The method of claim 1, wherein the background fluorescence is expressed as an empirical equation, and wherein the empirical equation comprises a Lorentzian fit, a Gaussian fit, or a polynomial fit.

6. The method of claim 1, further comprising administering a contrast agent into a scattering medium.

7. The method of claim 1, wherein reconstructing the image comprises summing together the processed image frames to generate a composite image.

8. The method of claim 1, further comprising using a noise reduction algorithm prior to or as a part of image reconstruction.

9. The method of claim 1, wherein acquiring the image frames corresponding to the two or more scan steps comprises moving the illumination source relative to the subject while acquiring the image frames.

10. The method of claim 1, wherein acquiring the image frames corresponding to the two or more scan steps comprises moving the subject relative to the illumination source.

11. The method of claim 1, wherein acquiring the image frames comprises descanning the image frames corresponding to the two or more scan steps.

12. The method of claim 1, wherein reconstructing the image comprises summing up the one or more processed image frames.

13. A fluorescence imaging system for generating an enhanced image of a target in a subject, comprising:
- a source configured to illuminate at least a portion of a surface of the subject by a patterned illumination at one or more scan steps;
- an imaging detector configured to acquire image frames at one or more scan steps, wherein the imaging detector is configured to collect emitted light from an illuminated region as well as from an area of interest away from the illuminated region; and
- an imaging processor configured to process the image frames to deduct a background fluorescence from the image frames and reconstruct an image of the target using the processed image frames, wherein the background fluorescence is based on an excitation spread function.

14. The system of claim 13, wherein the imaging detector is a one dimensional detector.

15. The system of claim 13, wherein the imaging detector is selected from a group consisting of a charged coupled device, an intensified charged coupled device, a time-gated charged coupled device, a gain-modulated charged coupled device, a complementary metal oxide semiconductor device, an electron bombardment charge coupled device, and an image intensifier tube.

16. The system of claim 13, wherein the source comprises a substantially monochromatic light source.

17. The system of claim 13, wherein the source comprises a continuous wave light source, a pulsed laser, a frequency modulated light source, an intensity modulated light source, a phase varying light source, or combinations thereof.

18. The system of claim 13, further comprising an illumination deflection device for directing the patterned illumination onto the surface of the subject.

19. The system of claim 18, wherein the illumination deflection device is in operative association with the detector to enable a descanned arrangement.

20. The system of claim 13, further comprising collection optics for directing the emitted light to the detector.

* * * * *